United States Patent [19]

Sheridan et al.

[11] Patent Number: 4,852,564

[45] Date of Patent: * Aug. 1, 1989

[54] FLEXIBLE CONNECTORS FOR MEDICO-SURGICAL TUBES

[75] Inventors: David S. Sheridan, Argyle; Isaac S. Jackson, Greenwich, both of N.Y.

[73] Assignee: Sheridan Catheter Corp., Argyle, N.Y.

[*] Notice: The portion of the term of this patent subsequent to Jun. 10, 2003 has been disclaimed.

[21] Appl. No.: 243,219

[22] Filed: Sep. 14, 1988

Related U.S. Application Data

[63] Continuation of Ser. No. 625,837, Jun. 28, 1989, abandoned.

[51] Int. Cl.$^4$ .............................................. A62B 9/09
[52] U.S. Cl. ........................... 128/202.27; 128/201.18; 128/912; 604/283; 604/281; 138/119; 138/121; 138/173; 138/DIG. 8; 285/122; 285/223
[58] Field of Search .................. 128/207.14, 207.15, 128/200.26, 207.18, 202.27, 201.11, 912; 604/280-284; 138/119-122, 172, 178, DIG. 5, DIG. 8, DIG. 11; 4/207; 285/DIG. 19, 122, 223, 224, 226, 227

[56] References Cited

U.S. PATENT DOCUMENTS

| 3,388,705 | 6/1968 | Grosshandler | 128/912 |
| 3,409,224 | 11/1969 | Harp et al. | 138/121 |
| 3,599,642 | 8/1971 | Tindel | 128/207.15 |
| 3,860,978 | 1/1975 | Wirth | 4/207 |
| 3,873,137 | 3/1975 | Yamaguchi | 285/226 |
| 3,924,165 | 12/1975 | Diebolt et al. | 138/121 |
| 4,050,466 | 9/1977 | Koerbacher | 128/207.15 |
| 4,275,724 | 6/1981 | Behrstock | 604/281 |
| 4,340,089 | 7/1982 | von Arnim et al. | 138/121 |
| 4,385,629 | 5/1983 | Wolf, Jr. et al. | 128/912 |
| 4,416,273 | 11/1983 | Grimes | 604/283 |

FOREIGN PATENT DOCUMENTS 1584865 2/1981 United Kingdom ............... 285/226

Primary Examiner—Max Hindenburg
Assistant Examiner—K. M. Reichle
Attorney, Agent, or Firm—Burns, Doane, Swecker & Mathis

[57] ABSTRACT

Proximal end connector units, by which medico-surgical tubes may be attached to breathing circuits or like fluid flow devices in a manner that mitigates interference with operations being performed on patients intubated with the MS tubes, comprising a straight, rigid, cylindrical distal end portion, a straight, rigid, cylindrical proximal end portion, a central tubular portion joining the distal end portion to the proximal end portion, the central tubular portion being bendable in an arc of at least 180° without diminution of its effective lumen, such proximal end portion, distal end portion and central tubular portion all being integral and formed of the same thin, plastic material, the central tubular portion comprising a plurality of circumferential, angular segments each consisting of a pair of sides that are of unequal length, the central tubular portion being compressed lengthwise by having the shorter side in each segment folded back under its longer side.

1 Claim, 2 Drawing Sheets

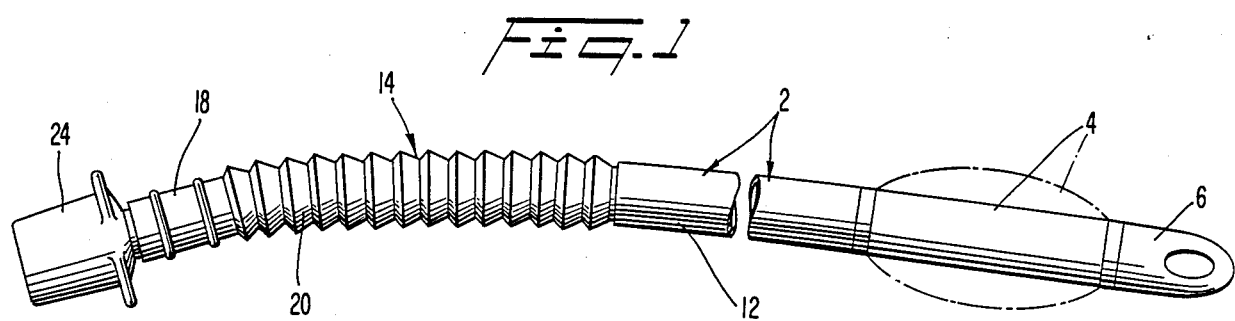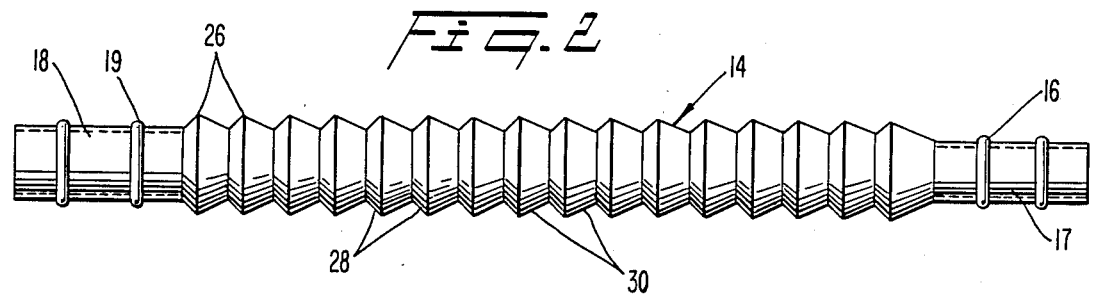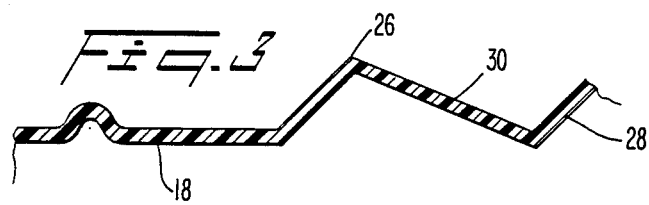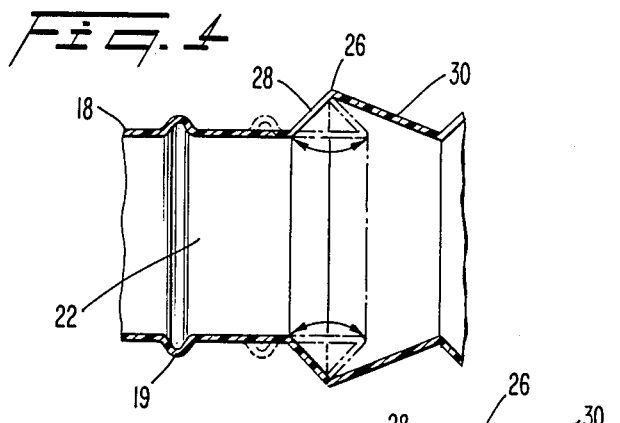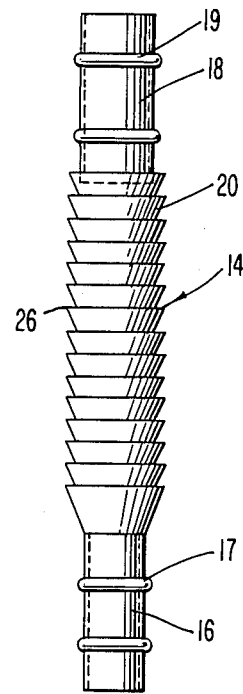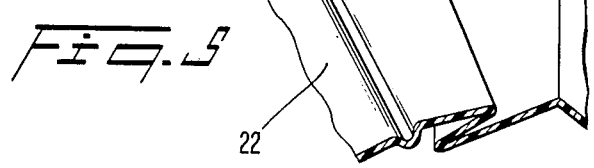

FLEXIBLE CONNECTORS FOR MEDICO-SURGICAL TUBES

This application is a continuation of application Ser. No. 625,837, filed 6/28/84, now abandoned.

BACKGROUND OF THE INVENTION

1. Field of the Invention

This invention relates broadly to medico-surgical tube devices. More particularly, it concerns improved connector units that may be fitted to proximal ends of medico-surgical tubes (MS tubes) so that the MS tubes may be attached to a fluid flow machines or other equipment in a manner that mitigates interference with operations being performed on patients intubated with the MS tubes.

2. Description of the Prior Art

Endotracheal tubes are typical of MS tubes that must be attached to fluid flow machines in order to function in treatment of patients in their intended manner. Numerous other MS tubes require connection to fluid flow machines in order to function, e.g., catheters, sump drain tube, thoracic catheters and the like. This invention provides new forms of connector units that may be used with all forms of MS tubes that require connection to associated fluid flow equipment.

Typical endotracheal tubes are arcuate in shape (bowed) to facilitate intubation of patients, for example, see U.S. Pat. Nos. 3,599,642 and 3,848,605. When such tubes have been properly positioned in the trachea, they assume the anatomical shape.

Conventionally, endotracheal tubes have a 15.0 mm coupler which adapts them to a breathing circuit which, in turn, connects to a ventilator. The breathing circuit usually consists of two thin wall, corrugated, flexible tubes, usually about 1.25" in diameter. Both are brought to the tracheal tube and joined to it through the 15.0 mm coupler. The position of this rather bulky breathing circuit can create complications for the surgeon operating on the intubated patient.

Some pre-shaped endo tubes have been manufactured for nasal and oral use. Such tubes for oral use have a bend at the point where the tube exits from the patient's mouth to make the tube extend down across the patient's chin.

Alternatively, such tubes for nasal use have a bend where the tube exits from the patient's nose to take the tube back over the forehead of the patient (see U.S. Pat. No. 3,964,488). However, tubes of these types have the disadvantage of being limited to the two stated directions and the permanent bends in the tubes limit the anesthetists' ability to position the distal end in the trachea.

Other ways of getting the proximal end of MS tubes adn connection elements out of the way of a surgeon have been developed. For example, one approach is to provide a metal coupler shaped to bend down over the chin of a patient when attached to the proximal end of a conventional tracheal tube (see U.S. Pat. No. 2,912,982). Also, central portions of MS tubes have been provided with corrugations to create sections therein that can be bent without kinking the tubes thus enabling the tubes to be shaped to bend in a desired direction (see U.S. Pat. Nos. 4,050,466 and 4,275,724). Yet another approach has been to provide adapters having a flexible, bellows like portion to be attached to the proximal end of MS tubes to provide a bendable connection between the MS tubes and anesthesia machines (see U.S. Pat. No. 3,388,705).

The present invention provide a further solution to the problems experienced in the use of MS tubes as discussed above that permits hospitals to stock only the commonly used type of MS tubes, i.e., it eliminates the need to stock special bend tubes. Also with the improved connector units of the invention, compound bends and directions are easily accomplished. In addition, the new connector units lock into a set shape so that there is no side thrust as can be caused by a resilient bellows type connector such as disclosed in U.S. Pat. No. 3,388,705. Hence, the patients, the anesthetists, the surgeons and the hospitals all benefit from the unique improvements provided by the invention.

OBJECTS

A principal object of the invention is the provision of new, improved forms of flexible connector units for application to the proximal ends of MS tubes. Further objects include the provision of:

1. Proximal end connector units for MS tubes that permit the tubes to be connected to breathing circuits in a manner that mitigates interference with operations being performed on patients intubated with the tubes fitted with such connector units.

2. Such connector units that permit compound bends on the proximal end portions of MS tubes to be easily accomplished.

3. Connector units for MS tubes that enable hospitals to stock a minimum number of different type MS tubes for intubations of patients.

Other objects and further scope of applicability of the present invention will become apparent from the detailed description given hereinafter. It should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

These objects are accomplished in accordance with the present invention by the provision of improved proximal end connector units (PECU) for use with MS tubes to enable connection of the tubes to external fluid flow equipment. Such PECU comprise a straight, rigid, cylindrical distal end portion having an I.D. equal to the diameter of the major lumen of the tracheal tube, a straight, rigid, cylindrical proximal end portion having an I.D. different from the I.D. of the distal end portion, and a central tubular portion joining the distal end portion to the proximal end portion, the central tubular portion being bendable in an arc of at least 180° without diminution of its effective lumen. The proximal end portion, distal end portion and central tubular portion of the PECU are all integral and formed of the same thin, plastic material. The central tubular portion comprises a plurality of circumferential, angular segments each consisting of a pair of sides that are of unequal length, the central tubular portion being compressed lengthwise with the shorter side of each of the pair being folded back under the longer side.

In a preferred embodiment, the new PECU have a 15.0 mm coupler member inserted in their proximal end portion. Such coupler member comprises a tapered, male distal end portion that is inserted into the PECU and a 15.0 mm male proximal end portion.

In a further embodiment, the cylindrical distal end portion of the PECU has a plurality of spaced apart, annular, integral beads, barbs or the like molded therein. Also, the cylindrical proximal end portion has at least one annular, integral bead, barb or the like molded therein. These annular portions provide stiffness and radial strength to the distal and proximal end portions of the PECU.

In yet another embodiment, a coupler member is connected to the proximal end portion of the PECU, which coupler member comprises a male or female proximal end portion and a female distal end portion that surrounds the cylindrical proximal end portion of the PECU and has a shoulder in its inner surface into which there is snapped an annular ring formed on the end of the cylindrical proximal end portion of the PECU.

Also in preferred embodiments, the shorter side of each of the pair of sides of each angular segment in the PECU is the proximal side of said segments.

BRIEF DESCRIPTION OF THE DRAWINGS

A more complete understanding of the present invention may be obtained by reference to the accompanying drawings in which:

FIG. 1 is a lateral view of an endotracheal tube equipped with a PECU made in accordance with the invention.

FIG. 2 is a lateral view of a endotracheal tube connector unit made in accordance with the invention as it is removed from the forming mold.

FIG. 3 is a enlarged, fragmentary, sectional view of a proximal end portion of the connector unit of FIG. 2.

FIG. 4 is another enlarged, fragmentary, sectional view of a proximal end portion of the connector unit of FIG. 2.

FIG. 5 is a view of the proximal end portion of FIG. 4 in a flexed or bent condition.

FIG. 8 is a lateral view of a connector unit like that shown in FIG. 2, but with such unit in a longitudinally compressed condition.

DESCRIPTION OF THE PREFERRED EMBODIMENTS

Figure 6:
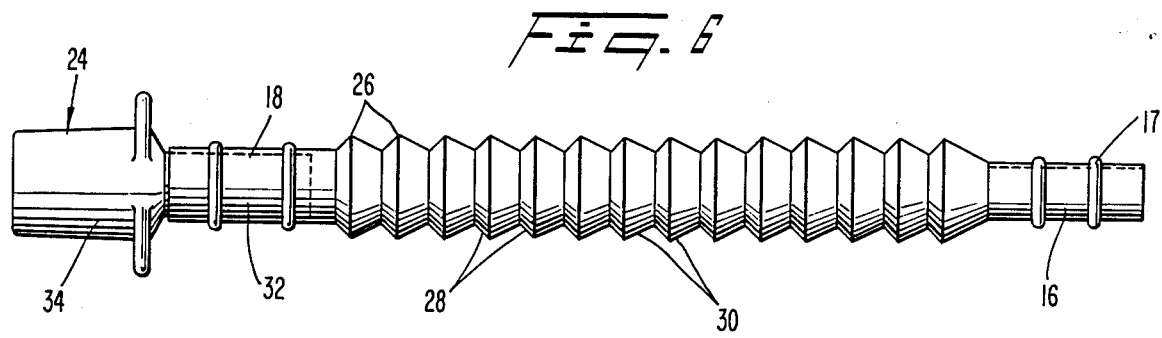
FIG. 6 is a view similar to FIG. 2 but with a coupler member fitted into the proximal end of the connector unit of FIG. 2.
Figure 7:
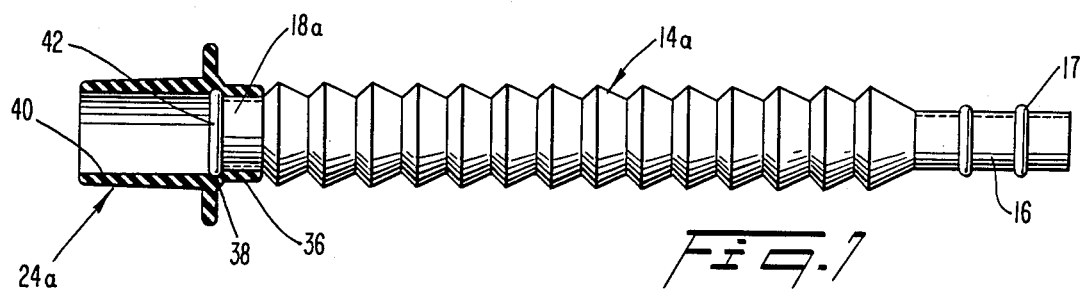
FIG. 7 is a view similar to FIG. 2 but with another type of coupler member fitted onto the proximal end of the connector unit of the invention.

With reference to the accompanying drawings in which identical items are identically numbered, a permanently bowed endotracheal tube 2 comprises an inflatable balloon cuff 4 on its distal end 6, a central major lumen and a secondary minor lumen (not shown) via which the cuff 4 can be inflated, a proximal end 12 through which the major lumen exits. The endo tube 2 is equipped with an improved PECU 14 of the invention for connection of the tube 2 to external fluid flow equipment (not shown).

The PECU 14 comprises a straight, rigid, cylindrical distal end portion 16 having an I.D. at least equal to the diameter of the major lumen 8, a straight, rigid, cylindrical proximal end portion 18 having an I.D. different from I.D. of the distal end portion 16, and a central tubular portion 20 joining the distal end portion 16 to the proximal end portion 18.

The central tubular portion 20 is bendable in an arc of at least 180° without diminution of its effective lumen which is at least equal to the lumen of the proximal end portion 18. The proximal end portion 18, distal end portion 16 and central tubular portion 20 are all integral and formed of the same thin, plastic material. The preferred plastic material is polypropylene with about a 75 shore D hardness, but other materials such as polyethylene, ABS, PVC, etc. may be used.

The proximal end portion has a lumen 22 sized to forceably accept a standard 15.0 mm coupler member 24.

The central tubular portion 20 of the unit 14 comprises a plurality of circumferential, angular segments 26 each of which consists of a short side 28 and a long side 30. FIG. 2 shows the unit 14 as it comes from the mold with each of the segments 26 extended. However, for use in the tube 2, the central tubular portion 20 of unit 14 is compressed lengthwise with the shorter side 28 of each segment 26 being folded back under the longer side 30. FIG. 4 shows by dotted lines and dimensional arrows the locking mode when compression takes place in the longitudinal direction. Each segment is deformed slightly as the short sides 28 are forced under the long sides 30 and as the short sides 28 pass center, each is firmly held. The compressed unit 14, as seen in FIG. 8, will stay locked in this compressed condition until it is forceably bent. At bending, the outside radius opens while the inside radius stays locked (see FIG. 4). This feature maintains the locked condition in the bent form. One segment bent as shown in FIG. 5 results in 20° to 30° of bend. FIG. 3 is a sectional view of one side of a segment 26 and shows the geometric arrangement of the locking feature.

Annular beads may be used to add stiffness and radial strength to to the proximal and distal end portions 18 and 16 of the unit 14. Thus, the cylindrical distal end portion 16 has a plurality of spaced apart, semicircular, integral, annular beads 17 molded therein. Additionally, the cylindrical proximal end portion 18 has at least one semi-circular, integral, annular bead 19 molded therein. The beads 17, in addition to adding stiffness and radial strength to the end portion 16, assist in holding the unit 14 locked into the proximal end 12 of the endotracheal tube 2. Alternatively, the portions 16 and 19 can be angular barbs (not shown).

The endotracheal tube 2 has a standard 15.0 mm coupler member 24 inserted in the proximal end portion 18 of the PECU 14. Such coupler member 24 comprises a tapered, male distal end portion 32 that is inserted into the PECU and an enlarged, male proximal end portion 34 (see FIGS. 1 and 6). In this assembly, the coupler member 24 is joined to the unit 14 by a press fit preventing any relative movement between the parts.

The PECU 14a may have another design of 15.0 mm coupler member 24a connected to their proximal end portion 18a. Such coupler member 24a comprises a female proximal end portion 34 and a female distal end portion 36 that surrounds the cylindrical proximal end portion 18a of the PECU 14a and has a shoulder 38 in its inner surface 40 behind which an annular ring 42 on the cylindrical proximal end portion 18a snaps to lock the member 24a to the unit 14a. Clearance between the coupler member 24a and PECU 14a permits the 15.0 mm coupler member to swivel freely. Medical grade grease is applied in the assembly of the parts to lubricate the parts connection and help to seal against gas leaks. The annular ring 42 is of barbed shape with its flat, distal side locking against a mating flat side of the shoulder 38 for safe retention of the coupler member 24a in the PECU 14a. The swivel arrangement as described relieves torque that may be introduced to the assembly by the breathing circuits (not shown).

Figure 10:
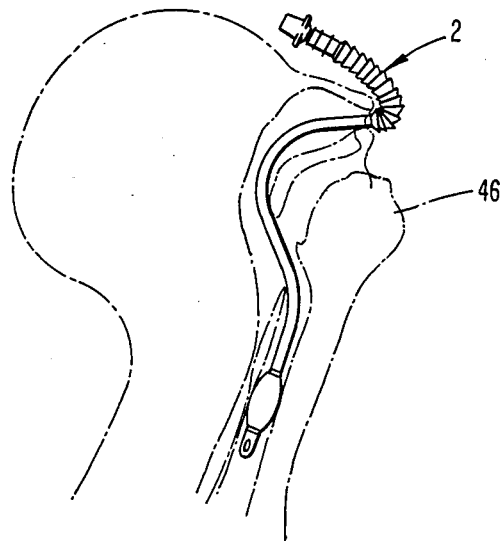
FIG. 10 is a schematic view of an endotracheal tube equipped with a PECU of the invention used in a typical nasal intubation of a patient.
Figure 9:
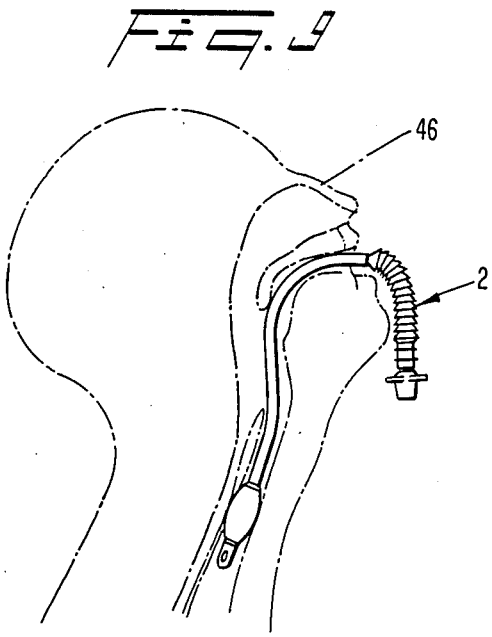
FIG. 9 is a schematic view of an endotracheal tube equipped with a PECU of the invention used in a typical oral intubation of a patient.

FIGS. 9 and 10 illustrate oral and nasal intubation respectively with endotracheal tubes equipped with PECU of the invention. They illustrate that in either case, the PECU 14 or 14a can be directed in any direction above the patient's face 46.

The new PECU of the invention are particularly useful with tracheal and tracheostomy tubes including both cuffed and uncuffed tubes. However, they are also useable with other types of MS tubes, e.g., catheters, sump drain tubes, etc. Tracheostomy tubes conventionally are supplied with a male 15.0 mm connector attached to the proximal end, so the new PECU of the invention for use with such tubes will have a 15.0 mm female coupler attached to the distal end and a 15.0 mm male coupler on the proximal end to connect to a fluid flow circuit.

The new PECU can advantageously be made in 15 different sizes and can be supplied with 15 different sizes of 15.0 mm couplers. The distal end of the PECU fits into the MS tube and its proximal end should be sized to a size that will accept the proper size fitting so that, in cases where a PECU is not used with a MS tube supplied with one of the new PECU, i.e. where th PECU is removed, the 15.0 mm coupler can be removed from the PECU and inserted directly into the MS tube.

Typically the new PECU can be made in sizes 3.0· mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm and 10.0 mm. Each of the different sizes will be different in diameter and length. Thus, as the size of the PECU gets smaller, the diameter and length are smaller.

The embodiments of the invention in which an exclusive property or privilege is claimed are defined as follows:

1. An improved proximal end connector unit for use in connection of a medico-surgical tube to external fluid flow equipment which comprises:

a straight, rigid, cylindrical distal open end portion having a first I.D., a straight, rigid, cylindrical proximal open end portion having a second I.D. different from said I.D. of said distal end portion, and a central tubular portion joining said distal end portion to said proximal end portion, said central tubular portion being bendable in an arc of at least 180° C. without any substantial diminution of its effective lumen which is at least equal to the lumen of said tube, said proximal end portion, distal end portion and central tubular portion all being integral and formed of thin, plastic material, said proximal end portion having an annular ring thereon, said central tubular portion comprising an integral plurality of segments each consisting of a first circumferential portion having an inner and an outer end and a second circumferential portion having an inner and an outer end, said second portion being of different length than said first portion, said circumferential portions being tapered in diameter from the outer ends to the inner ends and being joined together at said outer ends such that adjacent portions form an obtuse angle therebetween at their outer ends in an extended position and an acute angle in a compressed position where the first circumferential portion is displaced into the second circumferential portion, and said inner ends of said first circumferential portion of each segment being joined at its inner end to the inner end of a second circumferential portion of an adjacent segment, and a coupler member connected to said cylindrical proximal end portion of said connector unit comprising a female proximal end portion, a female distal end portion that surrounds said cylindrical proximal end portion and a shoulder in the inner surface of said female distal end portion into which is snapped said annular ring of said cylindrical proximal end portion, said shoulder and said annular ring being sized so that said coupler member may swivel freely on said connector unit without gas leakage through the junction between said shoulder and said annular ring.

* * * * *